United States Patent [19]

Halperin

[11] Patent Number: 5,003,982
[45] Date of Patent: Apr. 2, 1991

[54] DYNAMIC INDENTATION SYSTEM

[75] Inventor: Henry R. Halperin, Baltimore, Md.

[73] Assignee: Johns Hopkins University, Baltimore, Md.

[21] Appl. No.: 386,249

[22] Filed: Jul. 28, 1989

[51] Int. Cl.$^5$ ............................................. A61B 5/02
[52] U.S. Cl. .................................... 128/695; 128/739; 73/573
[58] Field of Search ............... 128/668, 695, 739, 740; 73/573, 579, 778, 788, 790, 807

[56] References Cited

PUBLICATIONS

Halperin et al., "Dynamic Transverse Stiffness Can Estimate Myocardial Wall Stress During Single Contractions", Physics in Medicine & Biology, 33 (Supl. I): 183, Aug. 1988.
Halperin et al., "Transverse Stiffness: a Method for Estimation of Myocardial Wall Stress", pp. 695–703, vol. 61, No. 5, Nov. 1987.

*Primary Examiner*—Randall L. Green
*Assistant Examiner*—Randy Shay
*Attorney, Agent, or Firm*—Banner, Birch, McKie & Beckett

[57] ABSTRACT

The dynamic indentation system cyclically indents a test material for the purpose of determining mechanical properties that cannot be measured directly, such as in-plane wall stress in intact hearts. A probe or an end surface thereof cyclically indents the test material while the indentation stress acting on the face of the probe and the position of the probe are measured. The indentations can be servo-controlled for added stability.

The transverse stiffness of the material is calculated as the slope of the relation between the indentation stress and indentation strain during each indentation cycle. The transverse stiffness is then used as an estimate of wall stress, and the relation between the transverse stiffness and in-plane strain can be used as a direct estimate of material properties.

The dynamic indentation system is suitable for estimating in-plane wall stress and material properties from different parts of a test material. Since the vibrations are high in frequency, any gross movement of the test material or of the probe during the period of one oscillation is very small and does not influence the transverse stiffness. The dynamic indentation system allows, for example, estimation of wall stress throughout the course of a single cardiac contraction.

12 Claims, 7 Drawing Sheets

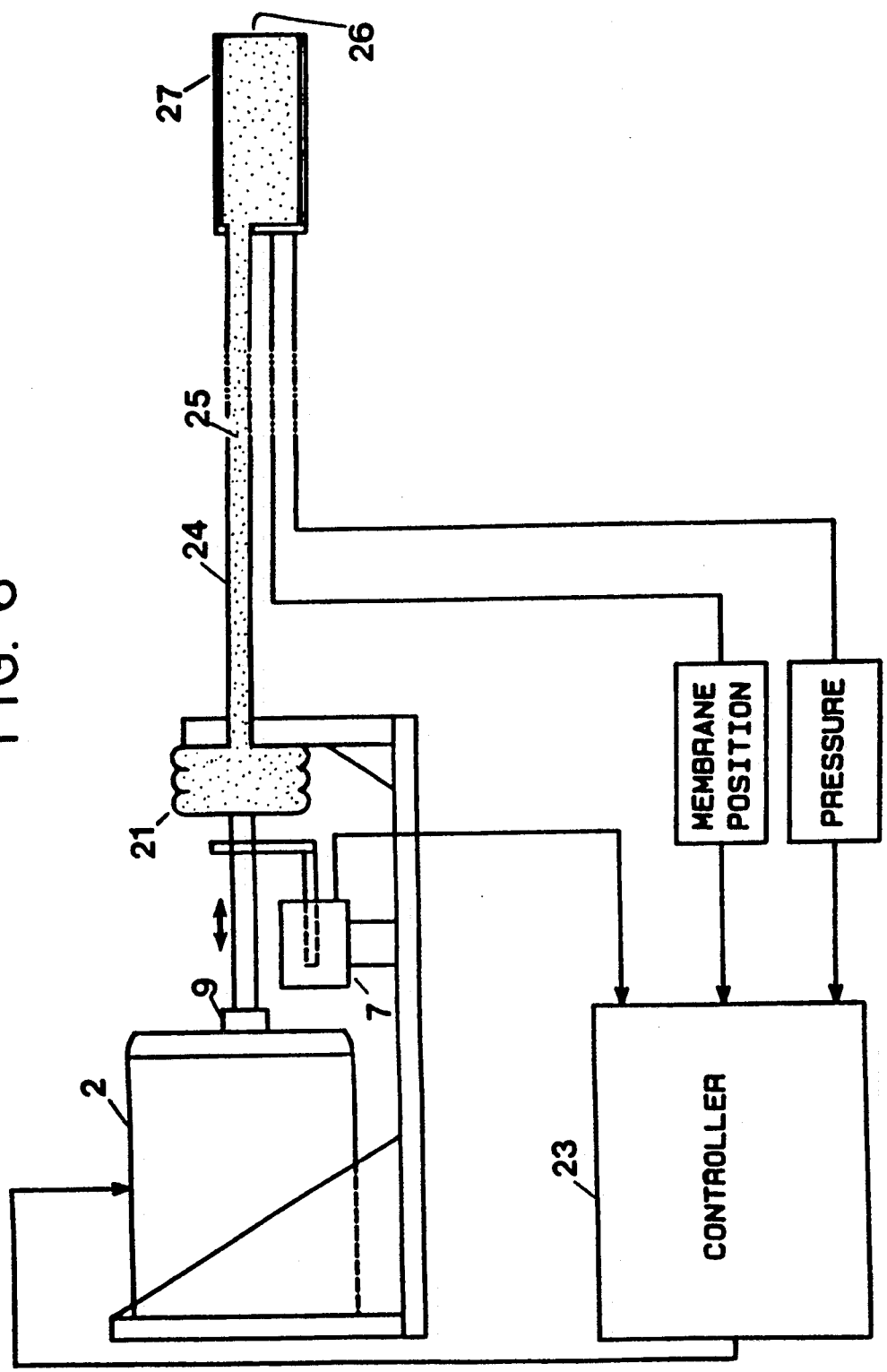

DYNAMIC INDENTATION SYSTEM

BACKGROUND OF THE INVENTION

1. Field of the Invention

The present invention relates to a system for estimating the mechanical properties of materials, e.g. for estimating stress and stiffness in cardiac muscle, with an indentation probe.

2. Description of the Related Art

The structural elements of animal and human bodies are made up of a wide variety of soft tissues, semi-hard cartilage, and hard bones. The structural integrity of these elements is crucial to the proper operation of the body. Unfortunately, analyzing these elements in a living body can be difficult due to limitations on isolation and analysis. Most diseases, such as heart disorders, are diagnosed by some method other than direct tissue examination.

The performance of an intact heart is manifested by its global generation of pressure and flow. This performance is the integrated effect of many factors including the geometry of the chamber, the mechanical properties of each region of the wall, the load imposed on each portion of the wall, and coronary blood flow. Global measurements, however, only describe overall cardiac performance.

There are difficulties in inferring regional changes, e.g. diseased heart soft tissue, from global measurements because there may not be a one-to-one relation between the regional function and the global measurements. Soft tissue abnormalities in one portion of the heart may be compensated for or overshadowed by load changes in another. Regional mechanics must be measured to differentiate whether regional dysfunction, myocardial infarct expansion, cardiomyopathy progression, and arrhythmia generation are due to changes in regional loading or to changes in regional mechanical properties.

Quantifying the regional properties of soft tissue, cartilage, or bone requires the measurement of regional wall strain and stress. In heart soft tissue, regional wall strain has been measured reasonably accurately in vivo [1–3]. The regional wall stress, however, is more difficult to quantify accurately.

Ascribing a value to the stress and stiffness of various areas in a heart is critical for determining the effects of regional stress loading and contractility to proper ventricular functioning. Without accurate measurements of stress, it is difficult to determine whether abnormal pump function is due to abnormal muscle that cannot generate stress or to normal muscle that is generating stress but is abnormally loaded. The ability to differentiate between these possibilities would have important diagnostic ramifications. This ability is hampered by the available measuring systems, however.

Strain gauge devices have been used to measure wall stress [4,5]. These devices give uncertain results because of the unknown degree of coupling between the transducer and ventricular wall [6,7]. Mathematical models have also been used to predict stress [8–10]. However, these models cannot be validated because there are no reliable actual measurements of wall stress for comparison [6].

A promising new approach has looked at the relationship between indentation stress and strain. It has been shown in the isolated ventricular septa that the ratio of indentation stress to indentation strain was proportional to the in-plane wall stress during steady-state indentations [11].

The apparatus used to measure the stress/strain relationship in the isolated ventricular septa consisted of two parts. The first component was a biaxial, servo-controlled system that allowed independent control of force and length in two orthogonal directions (x and y axes) in the plane of the septa. In-plane forces were measured by transducers connected to thread carriages supporting the septa.

The second component was the transverse indenter. The indenter included an arm along the z-axis that was mounted to allow visual detection of positional markers. The probe was about 7 mm in diameter. A z-axis force transducer was positioned on the arm. A stepper-motor was calibrated for measuring the z-axis displacement of the probe surface indenting the septa. As the probe indented the septum, the resulting force was measured by the z-axis force transducer. In-plane forces were measured by the in-plane force transducers.

Measurements from the indentation probe were taken at a variety of depths over a series of beats. At least 20 stable contractions were required to determine the transverse stiffness of the specimen. The transverse stiffness could be determined only every 20–40 seconds because the indenting probe had to be accurately positioned at 6–10 different depths in the muscle and maintained in a constant indenting angle at each depth for 2–3 cycles. This delay between successive readings makes it difficult to follow changes in wall stress over time. It was not possible to follow changes in the wall stress over a single contraction. Due to the relatively long measuring period, this form of measurement is best described as "steady state".

It would, therefore, be desirable to provide a device that could determine the transverse stiffness in a short enough period of time to allow estimation of wall stress throughout a cardiac contraction cycle. Preferably, such a device could make the transverse stiffness determinations from either the endocardial or epicardial surfaces of the heart and could be used percutaneously.

REFERENCES

1. Prinzen T, Arts T, Prinzen F, Reneman R: Mapping of epicardial deformation using a video processing technique. J Biomech, vol 19, pp 263–273, 1986.

2. Theroux P, Franklin D, Ross J, Kemper W: Regional myocardial function during acute coronary occlusion and its modification by pharmacological agents in the dog. Circ Res, vol 35, pp 896–908, 1974.

3. Walley A, Grover M, Raff G, Benge J, Hannaford B, Glantz S: Left ventricular dynamic geometry in the intact and open chest dog. Circ Res, vol 50, pp 573–589, 1982.

4. Feigl EO, Simon GA, Fry DL: Auxotonic and isometric cardiac force transducers. J Appl Physiol 23:597–600, 1967.

5. Burns JW, Covell JW, Myers R, Ross J Jr: Comparison of directly measured left ventricular wall stress calculated from geometric reference figures. Circ Res. 28:611–621., 1971.

6. Yin FCP: Ventricular Wall Stress. Circ Res. 49:829–842, 1981.

7. Huisman RM, Elzinga G, Westerhoff N, Sipkema P: Measurement of left ventricular wall stress. Cardiovasc Res 14:142–153, 1980.

8. Sandler H, Dodge HT: Left ventricular tension and stress in man. Circ Res 13:91–104, 1963.

9. Mirsky I: Effects of anisotropy and nonhomogeneity on left ventricular stresses in the intact heart. Bull Math Biophys 32:197-213, 1973.

10. Janz RF, Grimm AF: Finite-element model for the mechanical behavior of the left ventricle. Circ Res 30:244-252, 1972.

11. Halperin H, Chew PH, Weisfeldt ML, Sagawa K, Humphrey JD, Yin FCP: Transverse stiffness: A method for estimation of myocardial wall stress. Circ Res. 61(5):695-703, 1987.

SUMMARY OF THE INVENTION

It is an object of the invention to allow the estimation of wall stress during a single cardiac contraction cycle.

It is another object of the invention to provide a dynamic indentation system for determining the transverse stiffness of materials in as little as 10 msec.

In accordance with these and other objects that will become apparent from the description herein, the dynamic indentation system of the invention comprises:
 a probe having an indentation surface;
 displacement means coupled to said probe for repetitively displacing said indentation surface against a material at a rate of about 10 to about 150 Hz to induce stress in said material; and
 means for measuring said stress.

The dynamic indentation system according to the invention operates quickly and permits an estimation of soft tissue, cartilage, and/or bone material stress in vivo. The system permits a physician to investigate in more detail stress and strain related effects thereby increasing the accuracy of diagnosis and efficacy of corrective treatment.

BRIEF DESCRIPTION OF THE DRAWINGS

FIG. 6 is a schematic of a vibrating catheter probe system formed in accordance with the present invention.

DETAILED DESCRIPTION OF THE INVENTION

A wide variety of materials can be tested with the system according to the invention. Exemplary materials include soft tissues, cartilage, and bone. For convenience, the various aspects of the invention will be described with reference to muscle soft tissue in the heart.

A vibrating probe is the focus of the system of the invention. The vibrating probe desirably has an indentation surface operating at a small deflection amplitude, e.g. about 0.1-0.5 mm and is coupled to means for repetitively displacing the indentation surface at a frequency within about 10 to about 150 Hz, preferably about 20-50 Hz, to induce an indentation stress on a specimen, and means for measuring the indentation stress.

Preferred embodiments of probes according to the invention use a probe assembly that vibrates as an entire unit or includes a membrane stretched across a distal lumen of a probe housing as an indentation surface. Either system operates by vibrating the indentation surface at a specified rate. For the membrane, an oscillating pressure wave is applied in the lumen using a gas, e.g. air, or a liquid.

Movement of the indentation surface is controlled by a servo control system. A pressure transducer communicating with the indentation surface measures the pressure (force) required for indenting the specimen to a given depth. For a probe having a membrane indentation surface, the pressure transducer simply measures the pressure in the distal lumen. When the entire probe assembly vibrates as the indentation surface, a standard force transducer can be mounted on the indentation surface thereby directly measuring the indentation force.

When the probe tip is in contact with the specimen, e.g. a heart muscle, the pressure in the distal lumen required to effect a fixed depth of indentation is influenced by the material properties of the muscle, i.e. the pressure in the distal lumen increases as the muscle stiffness increases. Because the servo system maintains the amplitude of the membrane displacements at a constant level, the pressure needed to achieve a given level of displacement increases as the stiffness of the muscle increases. The pressure transducer reading, then, can be used as a level of the muscle stiffness.

A relatively high oscillation rate, e.g. within the range of about 10 to about 150 Hz, preferably from about 20 to 50 Hz is used to reduce the influences associated with any gross movement of the muscle or the probe during the testing cycle. This insensitivity to movement overcomes the problems associated with the prior apparatus and permits measurements to be made of living hearts. A probe according to the invention can be inserted through an opening in the chest cavity. Alternatively and even more preferably, the probe can be located within a catheter and moved directly into the suspected area of the heart by passage through an appropriate artery.

Figure 1:
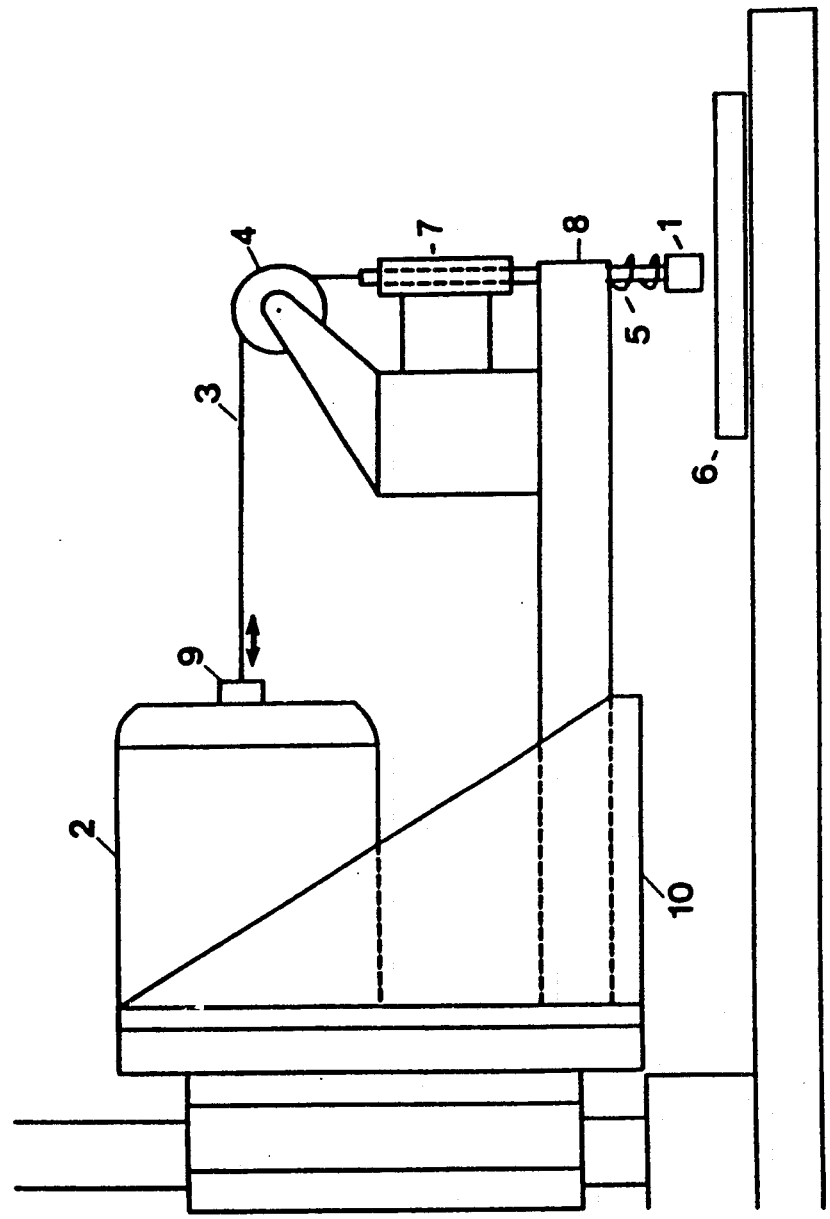
FIG. 1 is a schematic side view of a vibrating probe system formed in accordance with the present invention.

The apparatus shown in FIG. 1 exemplifies a device according to the invention. Similar elements found in other drawings are given the same reference number.

In FIG. 1, a combination indentation probe/transducer, referred to herein as probe 1, is moved by displacement means such as linear motor 2 coupled to probe 1 by cable assembly 3. The alignment of the cable can be changed by a device such as a pulley 4. A bias means such as spring 5 maintains tension on the cable and causes the probe to move as a unit toward test specimen 6. The indentation surface, therefore, is the distal end of probe 1. An alternative form of probe 1 uses a membrane across a distal end of probe 1 as the indentation surface. The membrane embodiment is described in more detail below with reference to FIGS. 6 and 7. As illustrated in FIG. 1, the entire probe assembly vibrates.

The position of probe 1 is measured by position measurement means such as position transducer 7. A preferred position transducer is a conventional linear variable differential transformer. A conventional force or pressure transducer, e.g. a Konigsburg, is mounted on the distal end of probe 1 so that the measuring surface of the transducer is the indentation surface of probe 1. The transducer measures the stress applied to test specimen 6 during the testing sequence. The lateral alignment of probe 1 is maintained by bearing 8.

Linear-motor 2 is of conventional design that is analogous to an audio speaker. As an example, Ling Dynamic Systems model 203 is particularly preferred. Briefly described, linear motor 2 comprises a movable coil suspended between the poles of a permanent magnet. Shaft 9 of linear motor 2 is connected to the movable coil. The position of the shaft is determined by the current flowing through the coil as well as the force acting along cable 3. As the coil moves, shaft 9 reciprocates in the direction shown by the arrows.

Figure 2:
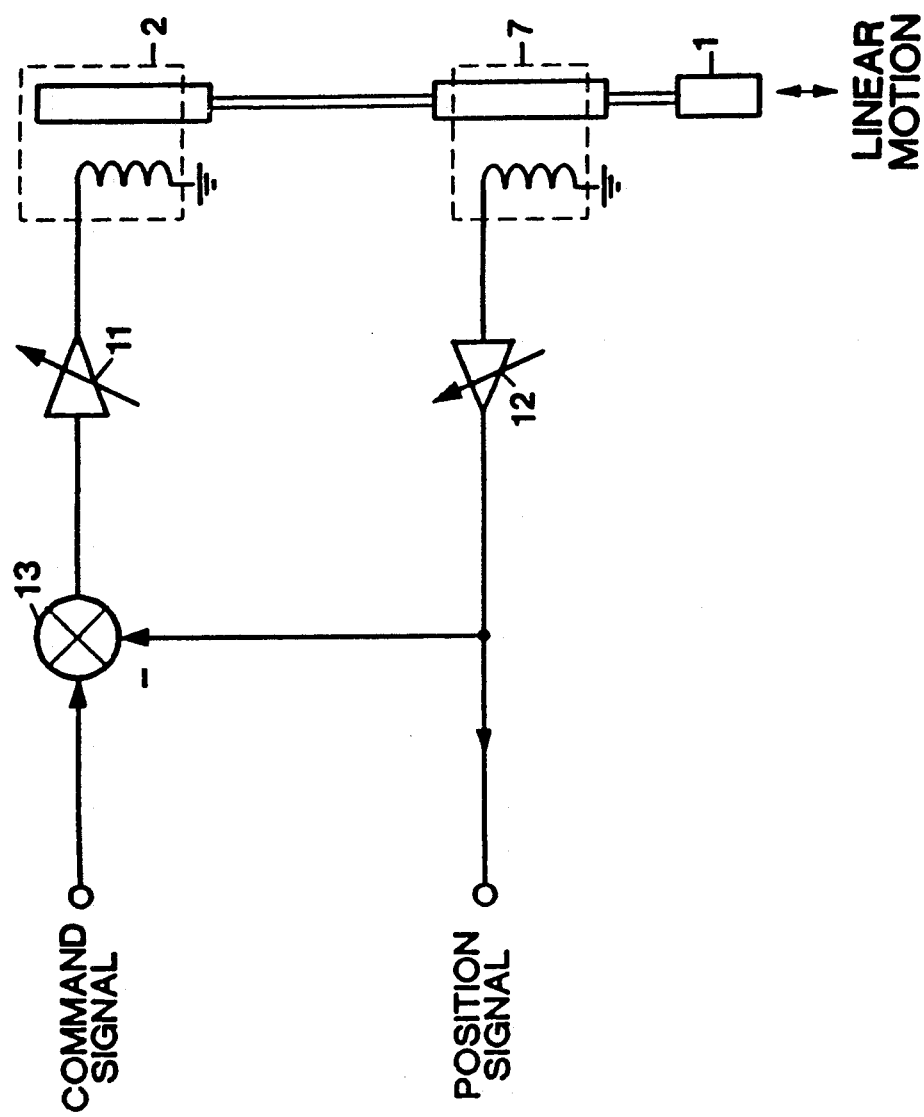
FIG. 2 is a schematic of the analog servo loop for assuring that the movement of the shaft of the linear motor follows the command signal.

Analog and digital servo-loops control the movement of the probe. As illustrated in FIG. 2, the analog loop minimizes the voltage difference between the position signal and the command signal thereby maintaining the indentation probe at the specified command position. The command signal comes from a controller, e.g. a microcomputer (not shown), and is applied to power amplifier 11. The amplified signal from power amplifier 11 drives linear motor 2.

The position of the shaft is measured by the position transducer 7. The position signal from position transducer 7 is amplified by amplifier 12 and applied to the differential amplifier 13 and the controller. Any difference between the position and command signals generates an error signal which is used to correct the drive signal to the linear motor 2 by appropriate error correction means. When the command signal and position signals are equal, the error signal will be zero and the linear motor is at the correct position.

A digital loop in the controller, e.g. a microcomputer, is used to produce the displacement oscillations of the probe about a specified position. For any desired frequency, a table is constructed in memory which contains information regarding amplitude versus time for a specified frequency.

The amplitude/time information is then read from the table at some reading rate. Reading rates are dependent on the system employed and can be at a wide variety of rates. A 2 kHz rate will be used for the description herein.

After all the amplitude/time values are read, the read sequence is repeated to synthesize a waveform. The waveform values are then multiplied by a calibration constant and added to a calibrated offset. When the resultant values are sequentially loaded into a digital-/analog converter, they produce calibrated oscillations of the indentation probe about a specified position. These displacement oscillations produce the cyclic indentations of the test specimen.

During the indentation period, the probe cyclically indents the test specimen more and then less deeply. The indentation stress accordingly increases to a maximum and then decreases to a minimum. Desirably, the probe maintains contact with the test specimen throughout the indentation cycle while maintaining the minimum indentation stress at a specified, nonzero level.

The whole vibrating probe assembly is attached to sliding platform 10 (FIG. 1) that can be moved vertically for optimal positioning of the probe.

Figure 3:
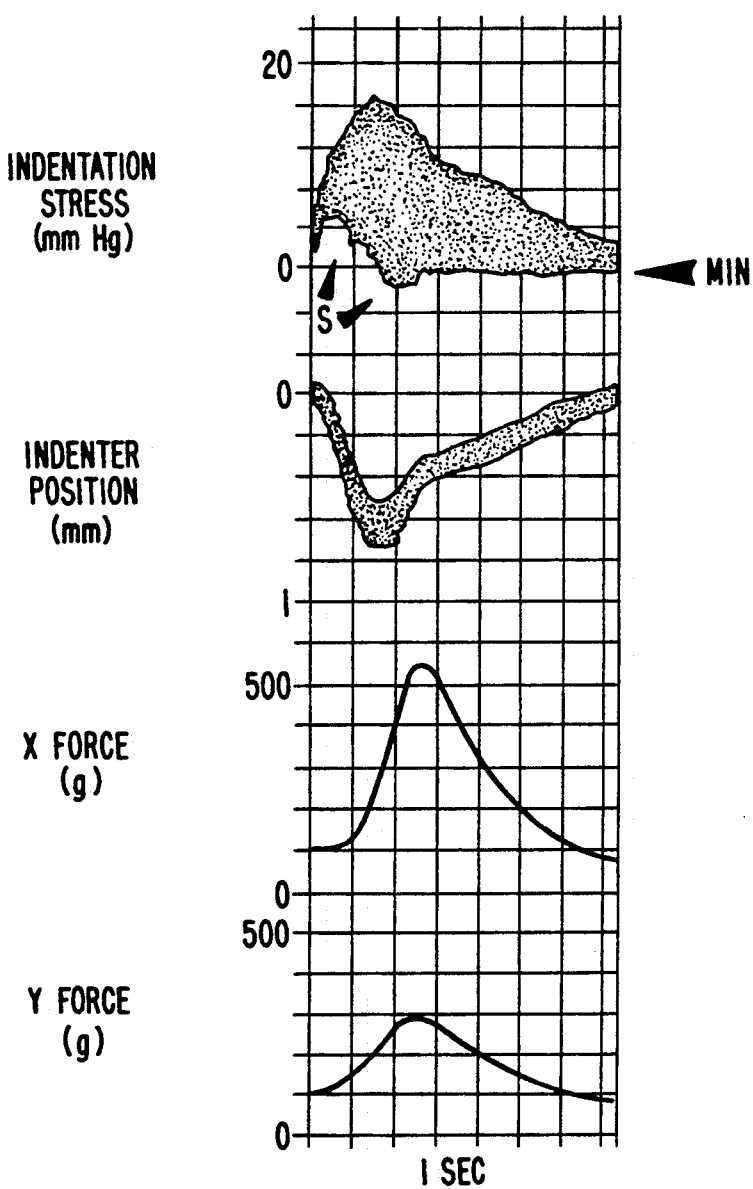
FIG. 3 is a record of indentation and in-plane data during a contraction of an isolated canine ventricular septum.

FIG. 3 graphically illustrates dynamic indentations during an active contraction in an isolated canine septum. As shown by the graphs, the amplitude of the 50 Hz indentations is 0.1-0.2 mm. A servo system moves the indenter to maintain the minimum indentation stress (MIN) at approximately 1-2 mm Hg. There is some servo error, S, since there is oscillation of the minimum value of indentation stress about the desired level. The zero position of the indenter is the diastolic thickness of the septum, and the positive direction is away from the septum. The X and Y forces are in the plane of the septum.

The controller digitizes the indentation stress and probe position signals at the same 2 kHz rate with an analog-to-digital converter. The minimum value of indentation stress is determined for each indentation cycle. If the minimum value is above the specified level, this indicates that the probe is indenting the muscle too deeply. The mean position of the probe is then moved away from the test specimen. Similarly, if the minimum value is below the specified level, the mean position of the probe is moved toward the test specimen (FIG. 3).

The amount that the mean position of the probe is moved during each subsequent indentation cycle is determined by the following equation:

$$dZ = K(f - fo)$$

where dZ is the amount of displacement, f is the minimum indentation stress measured during the previous indentation cycle, fo is the desired minimum indentation stress, and K is a constant (control gain).

The controller does not abruptly move the probe the desired dZ, since such abrupt motion tends to make the position control unstable. Instead, the probe is moved in increments over one indentation cycle time (20 ms for 50 Hz) with each increment occurring during successive 2 KHz sample times. During each increment of movement of the probe, preset limits are checked, and movement is stopped if those limits are reached. The limits include absolute limits on the position (maximum displacement is typically about 5 mm) as well as limits on dZ. If dZ is too large, the servo-control can be unstable.

Based on this control algorithm, the mean position of the probe is simply the sum total of the initial position selected by the user and all of the dZ, e.g., K times the integral of the minimum-stress errors. Integral regulators are preferred for control over the minimum stress.

Routine iterations are contemplated for optimizing the value of K for controlling the minimum indentation stress. An average value is first chosen and programmed into the control algorithm. This value is then refined in a few iterations to minimize the servo-error.

Once the indentation stress and indenter position are measured, the transverse stiffness is calculated as the slope of the relation between the indentation stress and indentation strain for each indentation cycle. The indentation stress is measured directly. The indentation strain is defined as the non-indented thickness of the specimen, minus the indented thickness, all divided by the non-indented thickness. The thickness can be measured using any known method of measuring wall thickness, such as M-mode measurements of echocardiography as discussed by Feigenbaum in Echocardiography, Lea & Febiger, Philadelphia, 1981, pages 129-130.

Figure 4A:
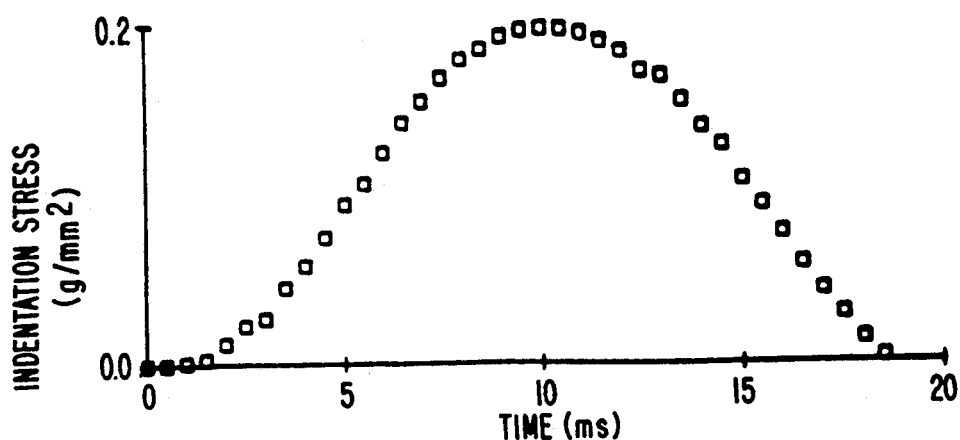
FIG. 4 is a record of indentation data during one indentation cycle and shows how the transverse stiffness is calculated.
Figure 4B:
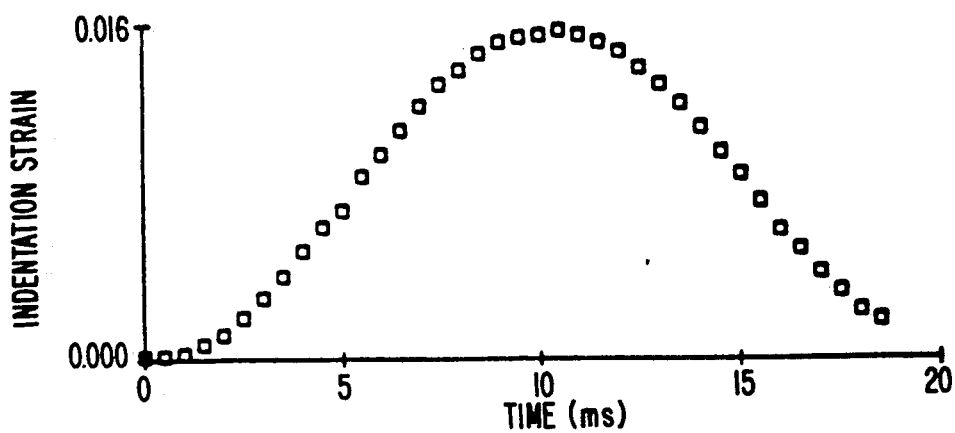
Figure 4C:
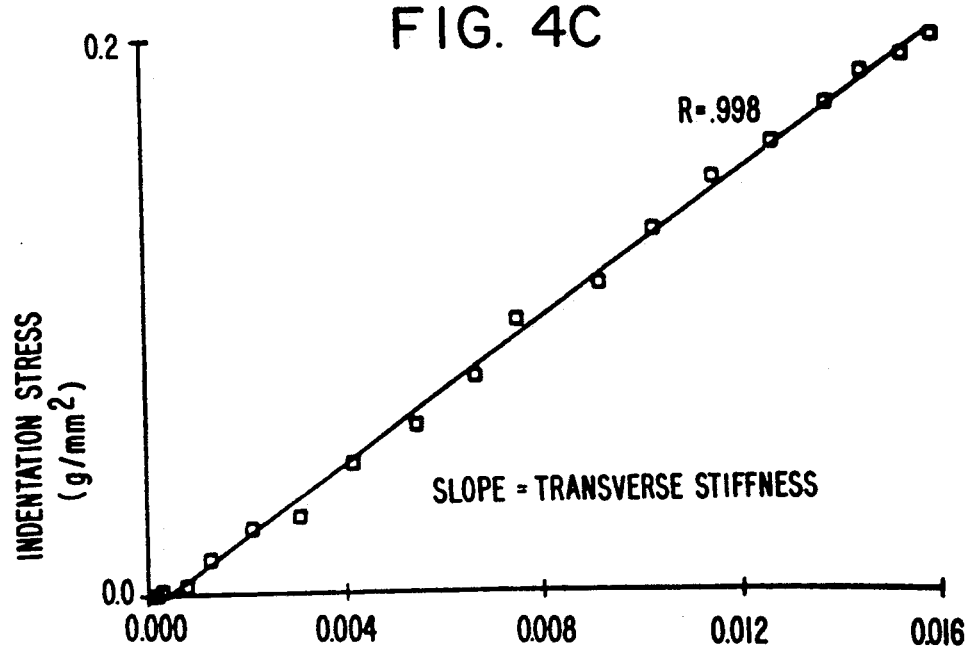

FIG. 4 shows the an example of the measured indentation stress (top panel) and indentation strain (middle panel) for one 50 Hz indentation cycle. The data were digitized at a 2 kHz rate. The slope of the relation between the indentation stress and indentation strain (bottom panel) is the transverse stiffness. Only data from the first half of the indentation cycle where the probe was moving toward the specimen was used in the illustrated data to calculate the transverse stiffness.

As a test of an entire vibrating probe assembly, the relationship between the dynamic transverse stiffness and the in-plane wall stress was studied in five isolated ventricular septa. The septal preparation consisted of canine hearts that were arrested with cold potassium cardioplegia. The left and right ventricular free walls were removed, leaving the interventricular septum. The septal artery was cannulated, and the septum was perfused with oxygenated fluorocarbon. The septa were then mounted in an apparatus that could apply biaxial in-plane strains, while measuring the resulting in-plane stresses [Ref 11]. The septa were effectively attached like a trampoline to two, orthogonal sets of carriages by loops of 3-0 silk thread.

In-plane force was measured by transducers coupled to the carriages, and in-plane length was measured between pairs of centrally placed carbon markers by two video analyzers. Isometric contractions were produced, and the in-plane stress at peak contraction was increased by stretching the specimen in steps under computer control. Each level of preload was maintained for two contractions. Eight increments of preload were studied in each specimen. Transverse indentations were performed on the central area of the specimen with peak displacements of 0.1-0.5 mm at frequencies of 20 Hz and 50 Hz.

The indentation stress was linearly related to the indentation strain, similar to FIG. 4, and the linear correlation was always high, with an average correlation coefficient of $0.98 +/- 0.03$. The slope of the relation between the indentation stress and indentation strain, i.e. the transverse stiffness, is, therefore, independent of the depth of penetrations for these small indentation strains. In addition, repeat determinations of transverse stiffness performed under identical loading conditions were always within 5% of each other.

Figure 5A:
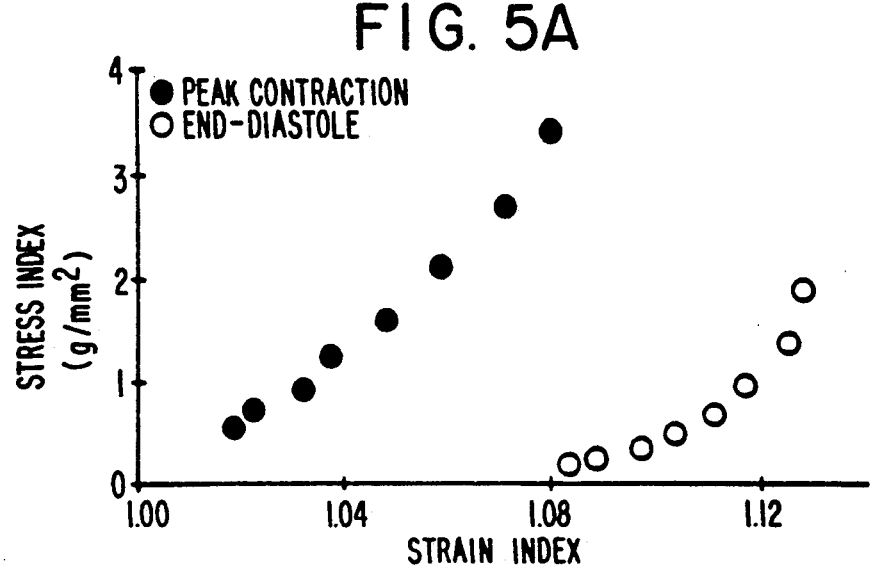
FIG. 5 is a plot of in-plane stress, in-plane strain, and transverse stiffness from peak systole and end diastole.
Figure 5B:
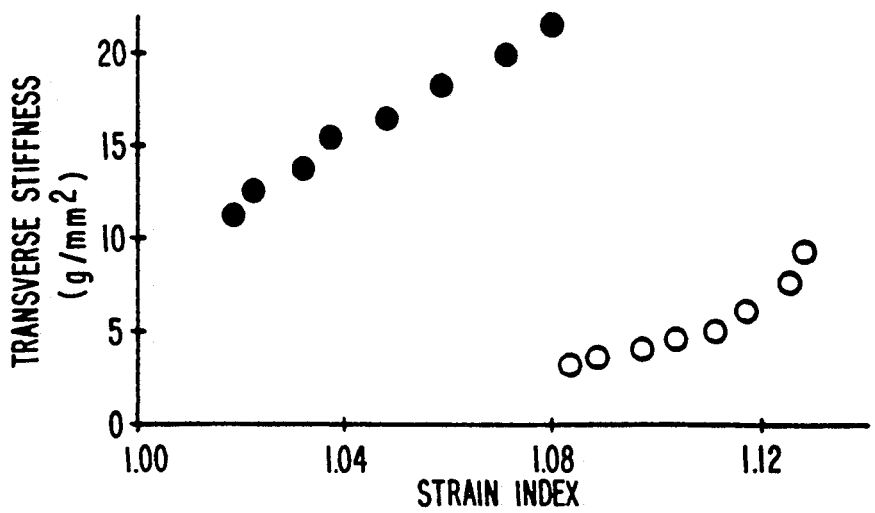
Figure 5C:
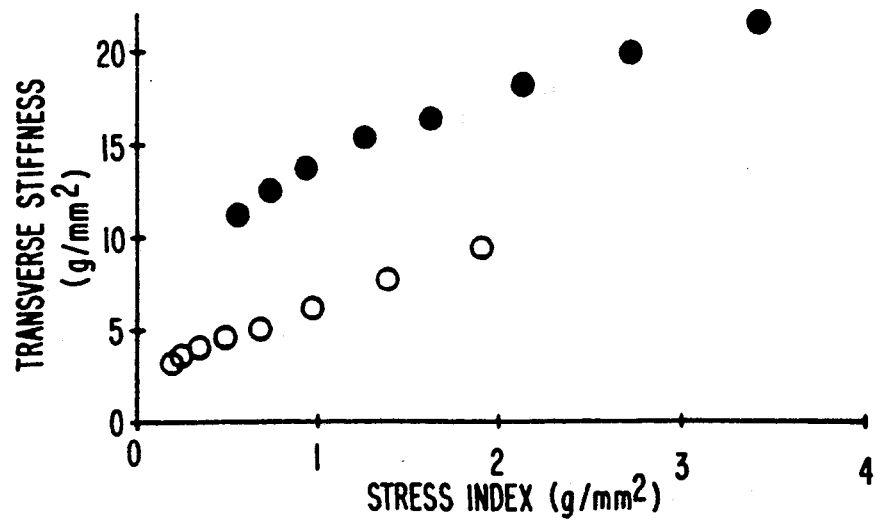

FIG. 5 shows the root-mean-square relationships [Ref. 11] between the in-plane stress index, the in-plane strain index, and the transverse stiffness for one of the stretching protocols. Each panel of FIG. 5 shows the relations at peak-contraction as well as at end-diastole.

The in-plane stress-strain relation at peak contraction is nearly linear as contrasted with the exponential stress-strain relation at end-diastole (upper panel). The relations between the transverse stiffness and the in-plane strain (center panel) are similar. Again, the relation at peak contraction is essentially linear while the relation at end-diastole is exponential. However, despite the different behaviors of the relations between the transverse stiffness and the in-plane strain, the relations between the transverse stiffness and in-plane stress (lower panel) are both nearly linear. This relation between the transverse stiffness and in-plane stress is consistent with earlier studies [Ref. 11] which used steady-state indentations.

Another preferred embodiment of the invention comprises a catheter probe which is suitable for indenting most of the epicardial and endocardial surfaces of the heart and for use percutaneously. A schematic of the vibrating catheter-probe system is shown in FIG. 6.

As illustrated in FIG. 6, linear motor 2 drives a bellow assembly 21. The position of shaft 9 is measured by position transducer 7. The direction in which shaft 9 moves is shown by the arrows. The linear oscillations of shaft 9 produce oscillations in volume and pressure in the bellows assembly 21. These pressure and volume oscillations are transmitted down connecting tube 24 through a gas or liquid coupling medium 25, resulting in displacement oscillations of membrane 26 covering the probe tip 27. Controller 23 receives the membrane position signals and, in real time, changes the amplitude of the signal driving the linear motor to produce constant amplitude displacement vibrations of the probe-tip membrane. The controller also records in real time the position of the probe-tip membrane as well as the pressure in the probe tip. A miniature version of the vibrating catheter probe having a diameter of about 1-3 mm can be inserted through a needle into an artery or vein and advanced into the heart chambers under fluoroscopic guidance. Once inside the heart chamber, the catheter probe can be positioned against different parts of the chamber wall to measure regional transverse stiffness. This allows measurement of transverse stiffness without opening the chest.

Accurate pressure measurements are possible with a number of commercially available miniature pressure transducers 28 (FIG. 7). The simplest method for determining the membrane position is to use the relation between the positions of the linear motor shaft and the membrane. If a non-compressible liquid is used to couple the motion and there is substantially no compliance in all of the connections, then there is a fixed amount of movement of the membrane for a given amount of travel of the linear motor shaft. In such instances, a position sensing device is not required in the probe tip, such as illustrated in FIG. 7A, but may be used to compensate for any inaccuracies that may be introduced such as when air is mixed in with the coupling liquid or if there is any significant compliance in the connections.

Figure 7A:
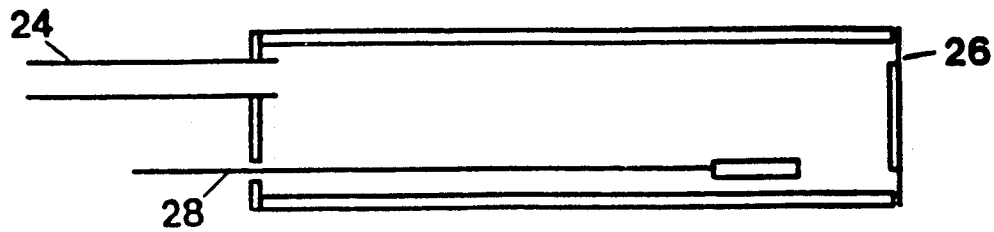
FIG. 7 is a schematic of vibrating catheter probe tip designs suitable for a catheter probe in accordance with the current invention.
Figure 7B:
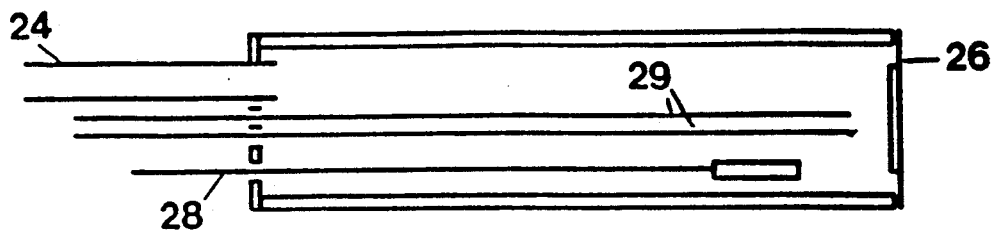

Another way that the position of the membrane can be determined is with an optically-based system such as illustrated in FIG. 7B. A light beam is directed onto membrane 26 by one of fiber optic tubes 29. The reflected light is directed onto a detector (not shown) by the second of fiber optic tubes 29. Using standard techniques, the position of the membrane is determined.

Figure 7C:
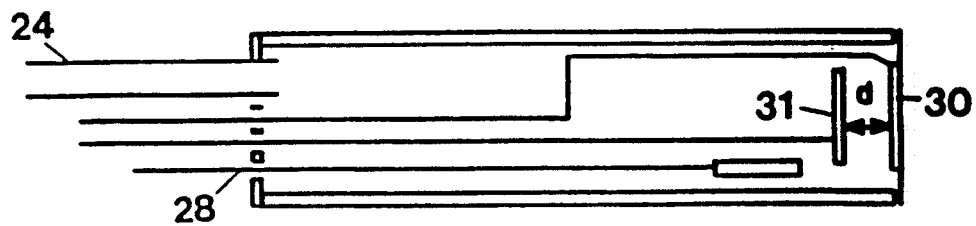

Another displacement measuring method is the capacitance-based method shown in FIG. 7C. A parallel-plate capacitor of approximately one pico-Farad capacitance is formed by membrane disk 30 attached to the vibrating membrane and stationary disk 31 located a few tenths of a millimeter from disk 30.

As the membrane vibrates, the capacitance of the parallel-plate capacitor changes. The change in capacitance is sensed by a conventional capacitance measuring device operating on the principle that the average displacement (d) of the membrane is proportional to the inverse of the capacitance.

The advantage of the capacitance-based method is that it will determine the average position of the membrane even if the membrane is distorted somewhat as it indents the muscle.

A preferred displacement measuring method is an electrical impedance based method, for which FIG. 7C is also applicable. In the impedance embodiment, a conductive fluid, e.g. physiologic saline (0.9% NaCl), fills the probe. The electrical impedance between the membrane-disk 30 and the stationary disk 31 is proportional to the length of the fluid column between the disks, which is simply the average distance between the disks.

The electrical impedance can be measured by applying a constant current oscillation of about 10-40 kHz between the disks and measuring the resultant voltage. The impedance will be the voltage divided by the current.

A more accurate measurement of impedance can be obtained by using a number of stationary electrodes, applying the constant current between pairs of the stationary electrodes, and measuring the resultant voltage between membrane-disk 30 and stationary disk 31. Any combination of stationary and membrane-disk electrodes can be used for the applied current and the resultant voltage determinations. In addition, an electrode or disk does not necessarily have to be attached to the membrane.

Figure 7D:
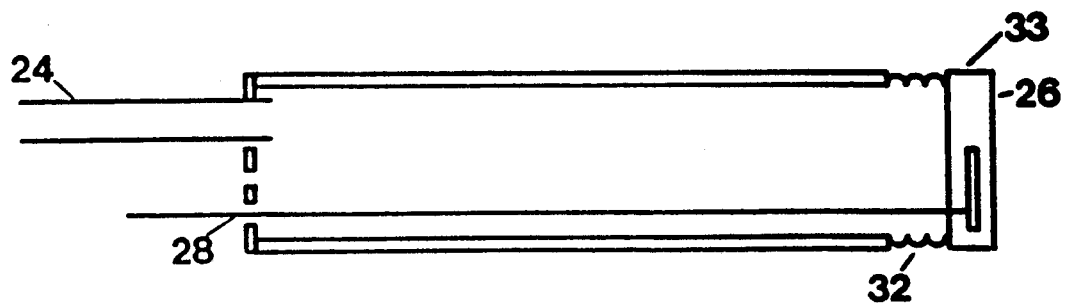

The vibrating catheter-probe tips schematically diagrammed in FIGS. 7A-C will give somewhat different indentation topographics than is obtained with a vibrating probe where the whole probe assembly vibrates. To have the vibrating catheter probe vibrate as a unit, a bellows containing probe tip can be used as depicted in FIG. 7D. In the latter configuration, pressure transducer 28 is mounted in small chamber 33. A membrane 26 covers the end of the chamber. The high frequency pressure oscillations in the vibrating catheter-probe tip move the whole chamber/membrane/pressure transducer assembly. The position of the chamber can be determined as described above or by the other means shown. Bellows 32 can be used to move the assembly or, alternatively, a small piston (not shown) can be used.

I claim:
1. A system comprising:
   a probe having an indentation surface;
   displacement means coupled to said probe for repetitively displacing said indentation surface at a rate of about 10 to about 150 Hz to induce a stress in said material; and
   means for measuring said stress.
2. A system according to claim 1 wherein said indentation surface comprises a membrane.
3. A system according to claim 1 wherein said indentation surface comprises an external distal end surface of said probe.
4. A system as in claim 1, wherein said displacement means comprises a linear motion motor.
5. A system as in claim 4, wherein said probe is coupled to said linear motion motor by a cable.
6. A system as in claim 1, further comprising:
   a linear bearing that constrains said probe to move in one direction, and means for measuring the position of said probe.
7. A system as in claim 1, wherein said means for measuring said stress comprises a force or pressure transducer.
8. A method for determining the stress of a material, said method comprising:
   indenting a material at a rate of about 10 to about 150 Hz to induce stress in a material; and
   measuring the stress in said material.
9. A method according to claim 8 wherein said material is soft tissue, cartilage, or bone.
10. A method according to claim 9 wherein said material is heart muscle.
11. A method according to claim 8 wherein the indenting step is at a rate of 20-50 Hz.
12. A method according to claim 8 wherein the indenting is by oscillating a membrane.

* * * * *

UNITED STATES PATENT AND TRADEMARK OFFICE
CERTIFICATE OF CORRECTION

PATENT NO. : 5,003,982

DATED : April 2, 1991

INVENTOR(S) : Henry Alperin

It is certified that error appears in the above-identified patent and that said Letters Patent is hereby corrected as shown below:

In column 1, before "Background of the Invention" please insert -- The invention described herein was made in the course of work under a grant or award from the Department of Health and Human Services.--

Signed and Sealed this

Twenty-eight Day of March, 1995

Attest:

BRUCE LEHMAN

*Attesting Officer*  *Commissioner of Patents and Trademarks*